(12) United States Patent
Chang et al.

(10) Patent No.: US 12,162,954 B2
(45) Date of Patent: Dec. 10, 2024

(54) METHOD FOR PREPARING ETELCALCETIDE HYDROCHLORIDE

(71) Applicant: KRISAN BIOTECH Co., Ltd., Tainan (TW)

(72) Inventors: Ya-Chun Chang, Tainan (TW); Shih-Wei Li, Tainan (TW)

(73) Assignee: KRISAN BIOTECH Co., Ltd., Tainan (TW)

( * ) Notice: Subject to any disclaimer, the term of this patent is extended or adjusted under 35 U.S.C. 154(b) by 0 days.

(21) Appl. No.: 17/866,905

(22) Filed: Jul. 18, 2022

(65) Prior Publication Data

US 2023/0043220 A1 Feb. 9, 2023

(30) Foreign Application Priority Data

Jul. 23, 2021 (TW) ................. 110127220

(51) Int. Cl.
*C07K 7/06* (2006.01)
(52) U.S. Cl.
CPC ..................................... *C07K 7/06* (2013.01)
(58) Field of Classification Search
None
See application file for complete search history.

(56) References Cited

U.S. PATENT DOCUMENTS

| | | | |
|---|---|---|---|
| 10,407,464 B2 | 9/2019 | Bezemer et al. | |
| 10,899,791 B2 | 1/2021 | Lee et al. | |
| 2015/0110820 A1* | 4/2015 | Laidler | A61P 37/08 424/185.1 |
| 2019/0352336 A1* | 11/2019 | Bezemer | C07K 1/1075 |

FOREIGN PATENT DOCUMENTS

| | | |
|---|---|---|
| CN | 109280078 A | 1/2019 |
| CN | 110054662 A | 7/2019 |
| CN | 112552376 A | 3/2021 |
| TW | 201915009 A | 4/2019 |
| WO | 2015154031 A1 | 10/2015 |

OTHER PUBLICATIONS

Martin et al. ('Greening the synthesis of peptide therapeutics: an industrial perspective' RSC Adv. V10 2020 pp. 42457-42492) (Year: 2020).*
Sikora et al. ('The role of counter-ions in peptides—an overview' Pharmaceuticals v13 2020 pp. 1-29) (Year: 2020).*

* cited by examiner

*Primary Examiner* — Ronald T Niebauer
(74) *Attorney, Agent, or Firm* — Joseph C. Zucchero; Carolyn S. Elmore; Elmore Patent Law Group, P.C.

(57) ABSTRACT

The present invention relates to a method for preparing etelcalcetide hydrochloride (etelcalcetide HCL). A first peptide is de-protected and cleaved from a solid support by a first solution system, for obtaining a second peptide, followed by coupling an activated L-Cys-OH to the second peptide in the second solution system for forming a TFA salt of etelcalcetide that is not or hardly dissolved in the second solution system. After purification by column chromatography, the TFA salt of etelcalcetide can be converted to etelcalcetide HCL using a third solution system that excludes hydrogen chloride during a real-time monitoring salt exchange step. The present method provides a simplified process and the etelcalcetide HCL with high purity and yield, for being advantageously applied in mass production of etelcalcetide HCL.

14 Claims, 2 Drawing Sheets
Specification includes a Sequence Listing.

METHOD FOR PREPARING ETELCALCETIDE HYDROCHLORIDE

RELATED APPLICATION

This application claims priority to Taiwan Application Serial Number 110127220, filed Jul. 23, 2021, which is herein incorporated by reference in its entirety.

SEQUENCE LISTING

The sequence listing submitted via EFS, in compliance with 37 CFR § 1.52(e)(5), is incorporated herein by reference. The sequence listing XML file submitted via EFS contains the file "SP-5391-US_SEQ_LIST_202312.xml", created on Dec. 12, 2023, which is 9,824 bytes in size.

BACKGROUND

Field of Invention

The present invention relates to a method for preparing calcimimetics. More specifically, the present invention to a method for preparing etelcalcetide hydrochloride (etelcalcetide HCl) with high purity and high yield.

Description of Related Art

Etelcalcetide is a calcimimetics (sensipar) and is used for treating secondary hyperparathyroidism (SHPT) in adult patients with chronic kidney disease (CKD), so as to suppress secretion of parathyroid hormone (PTH).

Etelcalcetide has a disulfide bond in its structure, and it will be hard to achieve ideal recovery rate and purity of the final product if etelcalcetide is subjected to reaction according to a conventional disulfide bond formation.

Therefore, there are several methods in the conventional processes in an attempt to solve the above-mentioned problems. A first process involves the solid-phase synthesis of a linear heptapeptide with a protecting group, followed by separation of the heptapeptide from the solid support (e.g., resin) and cleavage of the protecting group, activation of D-Cys (Pys) of the heptapeptide, reaction of the activated heptapeptide with L-Cys-OH to obtain TFA salt of etelcalcetide, and purification by column chromatography. Then, the TFA salt of etelcalcetide is subjected to a salt exchange step (or called as a step of converting salt), which is dissolved in a solution of 12 M hydrochloric acid and isopropyl alcohol (IPA) under low temperature, so as to obtain etelcalcetide hydrochloride (etelcalcetide HCl). The advantages of the first process are that the synthetization can be monitored, and a risk of degradation of the final product can be reduced since the final product is insoluble in IPA. However, the disadvantages of the first process are that a relatively time-consuming freeze-drying step (or called as lyophilization) must be performed twice, and the salt exchange step is required under low temperature.

A second process involves the solid-phase synthesis of a linear heptapeptide with a protecting group, followed by cleavage of the protecting group D-Cys of the heptapeptide from the solid support (e.g., resin), reaction of the heptapeptide immobilized on the resin with activated L-Cys-OH [e.g., Boc-L-Cys (NPys)-OH], separation of the octapeptide from the solid support (e.g., resin), cleavage of the remaining protecting groups to obtain TFA salt of etelcalcetide, and purification by column chromatography. Then, the TFA salt of etelcalcetide is subjected to a salt exchange step in the presence of aqueous solution of hydrochloric add (pH≥2), so as to obtain etelcalcetide HCL. The disadvantages of the second process are relatively time-consuming lyophilization at least thrice and incapable of real-time monitoring a part of the synthesis step and the salt exchange step.

A third process involves the solid-phase synthesis of a linear heptapeptide with a protecting group, followed by only cleavage of the protecting group D-Cys of the heptapeptide, activation of D-Cys (Pys) of the heptapeptide, and reaction of the activated heptapeptide immobilized on the resin with Boc-L-Cys-OH having a protecting group, so as to obtain TFA salt of etelcalcetide. Next, octapeptide is separated from a solid-phase support (e.g., resin), and the remaining protecting groups are cleaved, to obtain the TFA salt of etelcalcetide, and purification by column chromatography. The disadvantages of the third process are incapable of real-time monitoring a part of the synthesis step and no disclosure how to perform the salt exchange step.

A fourth process involves the solid-phase synthesis of a linear heptapeptide with a protecting group, followed by separation of the heptapeptide from the solid support (e.g., resin) and cleavage of the protecting group, activation of D-Cys(Scm) of the heptapeptide, and reaction of the activated heptapeptide with L-Cys-OH, so as to obtain TFA salt of etelcalcetide. Alternatively, the heptapeptide reacts with activated L-Cys(Scm)-OH, so as to obtain TFA salt of etelcalcetide. Later, the TFA salt of etelcalcetide is purified by column chromatography and converted to acetate (AcOH) salt of etelcalcetide, followed by elution in the presence of ammonium chloride and dilute hydrochloric acid, lyophilization at once, so as to obtain etelcalcetide HCl. The disadvantages of the fourth process are that an aqueous hydrochloric acid exists in the salt exchange step and there Is a risk of the aqueous hydrochloric acid potentially degrading the final product.

Hydrochloric acid is necessarily used in the salt exchange step of those conventional processes; however, there is a risk of hydrochloric acid for potential deamidation and degradation of the final product. Even the risk of degradation of the final product can be overcome, the salt exchange step cannot be monitored in real time. Therefore, there is an urgent need to improve the method for preparing etelcalcetide HCL, so that a process can provide etelcalcetide HCL with high purity, high yield and mass production, as well as the real-time monitoring salt exchange step.

SUMMARY

Accordingly, an aspect of the invention provides a method for preparing etelcalcetide HCL. A side-chain protecting group of a first peptide is cleaved with a first solution system, and the first peptide is separated from amide resin, and then the resultant second peptide and activated L-Cys-OH react with a second solution system, so as to obtain TFA salt of etelcalcetide. After purification by column chromatography, a real-time monitoring salt exchange step is performed on the TFA salt of etelcalcetide by using a third solution system, so as to obtain etelcalcetide HCL. Since the third solution system includes a chlorine-containing inorganic salt but excludes hydrochloric acid, the process can be simplified and provide the etelcalcetide HCL with high yield, thereby facilitating the mass production of etelcalcetide HCL.

Moreover, another aspect of the invention also provides a method for preparing etelcalcetide HCL. A coupling reaction is performed by using a second solution system, so that activated L-Cys-OH reacts with a second peptide without a side-chain protecting group, the obtained TFA salt of etelcalcetide Is subjected to a purification by column chromatography, and then a real-time monitoring salt exchange step is performed by using a third solution system, to obtain etelcalcetide HCL. Since the TFA salt of etelcalcetide is not or hardly dissolved in the second solution system, and the third solution system includes a chlorine-containing inorganic salt but excludes hydrochloric acid, impurities in the etelcalcetide HCL can be effectively reduced, thereby facilitating the mass production of etelcalcetide HCL.

According to the aforementioned aspect, the invention provides a method for preparing etelcalcetide HCL. In an embodiment, the method includes the following steps. At first, a solid-phase synthesis step is performed to obtain a first peptide shown in a formula (I) (SEQ ID NO:1), where a C terminal of the first peptide can be a resin-bound peptide, immobilized to amide resin, Ac of the formula (I) represents an acetyl group, X represents a first side-chain protecting group, and Y represents a second side-chain protecting group:

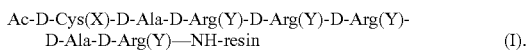

Ac-D-Cys(X)-D-Ala-D-Arg(Y)-D-Arg(Y)-D-Arg(Y)-D-Ala-D-Arg(Y)—NH-resin    (I).

Next, the first side-chain protecting group (X) and the second side-chain protecting group (Y) of the first peptide are cleaved with a first solution system, and the first peptide is separated from the amide resin, to obtain a second peptide shown in a formula (II) (SEQ ID NO:2), where the first solution system consists of TFA, TIS, EDT and water:

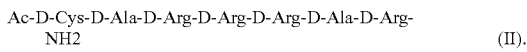

Ac-D-Cys-D-Ala-D-Arg-D-Arg-D-Arg-D-Ala-D-Arg-NH2    (II).

Then, a coupling reaction is performed by using a second solution system, so that L-Cys(Z)—OH is coupled to the D-Cys residue of the second peptide and a disulfide bond is formed, so as to obtain TFA salt of etelcalcetide (SEQ ID NO:3) where the TFA salt of etelcalcetide is not or hardly dissolved in the second solution system, and Z represents a side-chain activating group such as Pys. After purification by column chromatography, a real-time monitoring salt exchange step is performed on the TFA salt of etelcalcetide by using a third solution system, so as to obtain etelcalcetide HCL (SEQ ID NO:3), where the third solution system includes a chlorine-containing inorganic salt but excludes hydrochloric acid.

In the aforementioned embodiment, the first side-chain protecting group can be, for example, Trt, and the second side-chain protecting group can be, for example, Pbf.

In the aforementioned embodiment, the second solution system may include lower alkyl ether. In the above example, the lower alkyl ether may include, but is not limited to methyl tert-butyl ether (MTBE), diethyl ether (DEE), ethyl tert-butyl ether (ETBE) and tert-amyl methyl ether (TAME). In another example, the second solution system further Includes acetonitrile (ACN), a lower alcohol or any combination thereof. In the above example, the lower alcohol may Include, but is not limited to methanol, ethanol, 1-propanol, isopropanol (IPA), 1-butanol, 2-butanol and tert-butanol (TBA).

In the aforementioned embodiment, the second solution system can include a lower alkyl ether. In the above example, the lower alkyl ether can include but be not limited to methyl tert-butyl ether (MTBE), diethyl ether (DEE), ethyl tert-butyl ether (ETBE) and tert-amyl methyl ether (TAME). In another example, the second solution system further includes acetonitrile (ACN), a lower alcohol or any combination thereof. In the above example, the lower alcohol can include but be not limited to methanol, ethanol, 1-propanol, isopropanol (IPA), 1-butanol, 2-butanol and tert-butanol (TBA).

In the aforementioned embodiment, before the real-time monitoring salt exchange step, the TFA salt of etelcalcetide can be optionally subjected to a purification step by column chromatography.

In the aforementioned embodiment, based on an equivalent number of the third peptide [as shown in formula (111)] as 1, and the equivalent number of the chlorine-containing inorganic salt can be, for example, at least 1,500.

In the aforementioned embodiment, the chlorine-containing inorganic salt can include but be not limited to NaCl, KCl, CaCl$_2$ and NH$_4$Cl.

Ac According to another aspect, the invention provides a method for preparing etelcalcetide HCL. In an embodiment, the method includes the following steps. At first, a second peptide shown in a formula (II) (SEQ ID NO:2) is provided, where Ac of the formula (II) represents an acetyl group, and the second peptide is in a free form. Next, a coupling reaction is performed by using a second solution system, so that L-Cys(Z)—OH is coupled to the D-Cys residue of the second peptide and a disulfide bond is formed, so as to obtain TFA salt of etelcalcetide (SEQ ID NO:3), where the TFA salt of etelcalcetide is not or hardly dissolved in the second solution system, and Z represents a side-chain activating group such as Pys. And then, a real-time monitoring salt exchange step is performed on the TFA salt of etelcalcetide by using a third solution system, to obtain etelcalcetide HCL (SEQ ID NO:3), where the third solution system comprises includes a chlorine-containing inorganic salt, and the chlorine-containing inorganic salt includes NaCl, KCl, CaCl$_2$) and NH$_4$Cl but excludes hydrochloric acid.

In the aforementioned embodiment, between the coupling reaction and the real-time monitoring salt exchange step, the TFA salt of etelcalcetide can be further optionally subjected to a solid-liquid separation step and a purification step by column chromatography, so as to remove the second solution system and obtain the TFA salt of etelcalcetide, where the solid-liquid separation step can be, for example, a filtration step.

With application to the method for preparing etelcalcetide HCL of the present invention, in which the resulted TFA salt of etelcalcetide is not or hardly dissolved in the second solution system, and the TFA salt of etelcalcetide is converted to etelcalcetide HCL by using a hydrochloric acid-free third solution system. The present method provides a simplified process and the etelcalcetide HCL with high purity and yield, for being advantageously applied in mass production of etelcalcetide HCL.

It is to be understood that both the foregoing general description and the following detailed description are by examples, and are intended to provide further explanation of the invention as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1A:
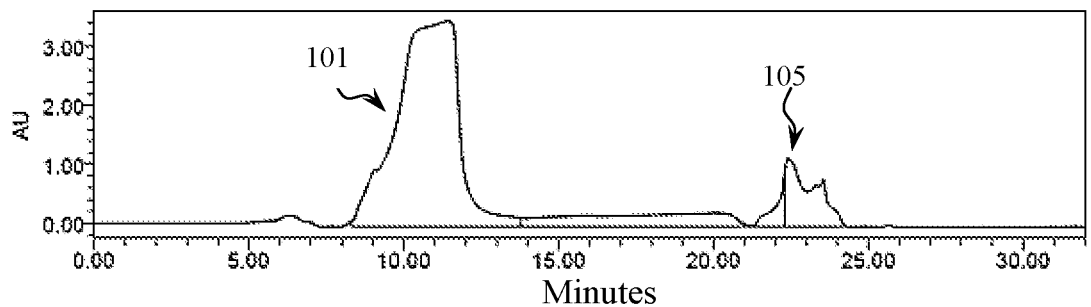
FIGS. 1A to 1C respectively illustrate the HPLC spectrogram of a real-time monitoring salt exchange step according to EXAMPLE 4-2 (FIG. 1A), Comparative EXAMPLE 4-1 (FIG. 1B) and Comparative EXAMPLE 4-2 (FIG. 1C) of the present invention.

If a term defined or used in a reference is inconsistent or opposite as it is defined or used herein, the definition of the term herein, other than that in the reference, is preferably applicable. Moreover, unless otherwise defined in the context, a singular term can include a plural one, and a plural term can also include a singular one. In addition, abbreviations used herein are listed in TABLE 1.

TABLE 1

| Abbreviation | Compound Name |
| --- | --- |
| ACN | Acetonitrile |
| AcOH | Acetic acid |
| Boc | Tert-butyloxycarbonyl |
| DEE | Diethyl ether |
| DIC | N,N'-diisopropyl-carbodiimide |
| DIPEA | N,N-diisopropyl-ethylamine |
| DMAc | N,N-dimethyl acetamide |
| DTT | Dithiothreitol |
| DPDS | 2,2'-dipyridyl-disulfide |
| EDT | Ethanedithiol |
| eq. | Equivalent |
| ETBE | Ethyl tert-butyl ether |
| Fmoc | 9-fluorenylmethyloxy-carbonyl |
| IPA | Isopropanol |
| Mmt | 4-methoxytrityl |
| MTBE | Methyl tert-butyl ether |
| NPys | 3-nitro-2-pyridine-sulfenyl |
| Oxyma | Ethyl cyano(hydroxyimino) acetate |

TABLE 1-continued

| Abbreviation | Compound Name |
| --- | --- |
| Pbf | 2,2,4,6,7-pentamethyl-dihydrobenzofuran-5-sulfonyl |
| Pys/SPy | 2-pyridinesulfenyl |
| Scm | S-carbomethoxy-sulfenyl |
| TAME | Tert-amyl methyl ether |
| TBA | Tert-butanol |
| TFA | Trifluoroacetic acid |
| TIS | Triisopropylsilane |
| TNBS | 2,4,6-trinitrobenzene-sulfonic acid |
| Trt | Trityl |

The "peptide" is used herein interchangeably with the term "polypeptide" and "protein" and refers to polymers of amino acids, which usually bind together by peptide bonds or disulfide bonds. "Peptide" also can be used in amino acids with one or more naturally occurring amino acid residues, or an amino acid polymer with the analogues or mimics corresponding to naturally occurring amino acids. "Peptide" further includes modified amino acid polymers such as glycoprotein with a carbohydrate residue, or phosphorylated peptide. The peptide, polypeptide and protein can be produced by liquid-phase synthesis, solid-phase synthesis or genetic engineering or recombinant cells.

The "amino acid" and "residue" referred to herein are interchangeable; and when used with peptide, they mean naturally occurring and synthesized amino acids, amino acid analogues, amino acid mimics, and non-naturally occurring amino acids that are chemically similar to the naturally occurring amino acids.

The "linear segment" and "linear chain" referred to herein are interchangeable, meaning that the main-chain structure of the peptide is a linear or straight chain, and the main chain can also include other branched structures depending upon actual requirements.

The "room temperature" referred to herein means a temperature of about 25° C.

As mentioned above, the present invention provides a method for preparing etelcalcetide HCL. A side-chain protecting group of a first peptide shown in a formula (I) (SEQ ID NO:1) is removed by using a first solution system, and the first peptide is separated from amide resin, then activated L-Cys-OH is coupled to a second peptide shown in a formula (II) (SEQ ID NO:2) by using a second solution system, to obtain TFA salt of etelcalcetide, and the TFA salt of etelcalcetide is subjected to a real-time monitoring salt exchange step by using a third solution system, to obtain etelcalcetide HCL shown in a formula (III) (SEQ ID NO:3):

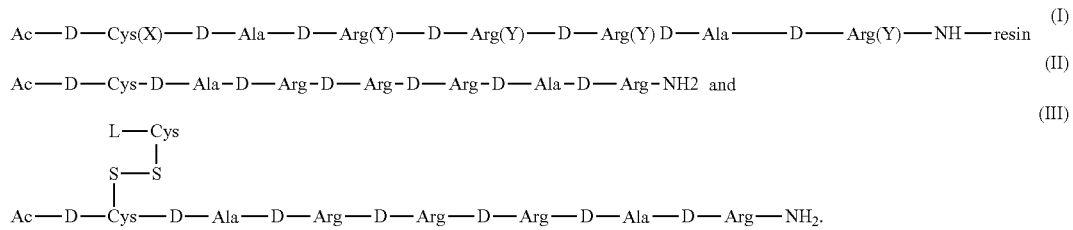

Specifically, in an embodiment, the aforementioned method for preparing etelcalcetide HCL can include the following steps. At first, a solid-phase synthesis step is performed, to obtain a first peptide shown in the formula (I). In the solid-phase synthesis step, a C terminal of the first peptide can be immobilized to a solid-phase support by using a conventional process, where the solid-phase support can be, for example, commercially available amide resin, such as Rink Amide MBHA resin and Rink Amide AM resin, rather than being limited thereto in the present invention.

In the aforementioned embodiment, Ac of the formula (I) represents an acetyl group, X represents a first side-chain protecting group, and Y represents a second side-chain protecting group. In an example, the first side-chain protecting group (X) can be, for example, Trt, and the second side-chain protecting group (Y) can be, for example, Pbf. Typically, the aforementioned protecting group is a protective group used in the technical field of peptide synthesis to protect the groups disturbing synthesis such as amino, carboxyl and sulfydryl groups on the main chains and side chains of amino acids, so as to prevent the amino, carboxyl, sulfydryl groups and the like from reacting and even generating impurities during the preparation of a final product, and the amino acid protected by the protecting group is referred to as "protected amino acid". The requirement for the aforementioned protection varies with the remote functionality and conditions of the preparation method. The requirement for the aforementioned protecting group can be easily acquired by a person with common knowledge in the technical field of the present invention. In respect of general description of the protecting group and use thereof, one can also refer to the textbooks in the technical field. Therefore, the side-chain structures of amino acid, appropriate side-chain protecting groups, a coupling mode of the protecting groups, an expression way of the amino acid with side-chain protecting groups and the like are not elaborated any more. For example, in Fmoc-D-Cys(Trt)-OH, Fmoc represents an N-terminal protecting group of amino acid, and Trt in the brackets represents a side-chain protecting group of Cys.

The obtained first peptide serves as a peptide precursor. Next, the first side-chain protecting group (X) and the second side-chain protecting group (Y) of the first peptide are removed by using a first solution system, and the first peptide is separated from the solid-phase support, to obtain a second peptide shown in the formula (II) (SEQ ID NO:2). In contrast to the first peptide in an immobilized form, the second peptide is in a free form, where the free form mentioned herein is defined when the second peptide is separated from the solid-phase support and the second peptide is not or slightly soluble in the second solution system. In this embodiment, the first solution system consists of TFA, TIS, EDT and water, and reacts for 1 to 5 hours (h) at room temperature, and then reacts preferably for 1.5 to 3 h, and more preferably for 2 h.

Next, a coupling reaction is performed in a second solution system, so that activated L-Cys(Z)—OH is coupled to the D-Cys residue of the second peptide and a disulfide bond is formed, to obtain TFA salt of etelcalcetide (SEQ ID NO:3), where Z represents a side-chain activating group such as Pys. In the embodiment, the second solution system can include a lower alkyl ether which can include but be not limited to methyl tert-butyl ether (MTBE), diethyl ether (DEE), ethyl tert-butyl ether (ETBE) and tert-amyl methyl ether (TAME). In other embodiments, the second solution system can further include acetonitrile (ACN), a lower alcohol or any combination thereof, where the lower alcohol can include but be not limited to methanol, ethanol, 1-propanol, isopropanol (IPA), 1-butanol, 2-butanol and tert-butanol (TBA). In some examples, the second solution system can only include MTBE. In some examples, the second solution system can consist of MTBE and ACN. In other examples, the second solution system can consist of MTBE and methanol. In still other examples, the second solution system can consist of MTBE and IPA. In the second solution system, a volume ratio of the lower alkyl ether to the ACN, or a volume ratio of the lower alkyl ether to the lower alcohol generally can be, for example, 1/1 to 5/1, and preferably 3/1 to 5/1. The TFA salt of etelcalcetide obtained in this way is not or hardly dissolved in the second solution system; before the real-time monitoring salt exchange step, the TFA salt of etelcalcetide is optionally subjected to a solid-liquid separation step, to easily remove the second solution system and obtain the TFA salt of etelcalcetide, where the solid-liquid separation step can include a filtration step. In other embodiments, between the coupling reaction and the real-time monitoring salt exchange step, the TFA salt of etelcalcetide is also optionally subjected to a solid-liquid separation step and a purification step by column chromatography, so as to remove the second solution system and obtain the TFA salt of etelcalcetide. It should be noted that, if the second solution system used a solvent instead of the lower alkyl ether, ACN and the lower alcohol as aforementioned, the TFA salt of etelcalcetide would raise problems of lower filtration efficiency, more difficult purification and the like.

In the aforementioned embodiment, before the coupling reaction, the method can further include a step of performing an activating reaction on L-Cys-OH, so as to obtain L-Cys (Z)—OH. It should be noted that, the coupling reaction excludes an activating reaction on the D-Cys residue of the second peptide because if the coupling reaction is changed into a way that the D-Cys residue of the second peptide is activated first, to, for example, form a D-Cys(Z) residue, and then L-Cys-OH is coupled to the D-Cys(Z) residue of the second peptide, a large number of byproducts will be produced, for example, part of the D-Cys(Z) residue of the second peptide will react with part of the D-Cys residue of the second peptide, and consequently, the purity and yield of the final product are significantly reduced, and even the original purpose cannot be achieved.

The resulted TFA salt of etelcalcetide can be subjected to a real-time monitoring salt exchange step by using a third solution system, so as to be converted to a pharmaceutically acceptable salt such as hydrochloride. In this embodiment, the third solution system includes chlorine-containing inorganic salt but excludes hydrochloric acid, where the chlorine-containing inorganic salt Includes NaCl, KCl, $CaCl_2$ and $NH_4Cl$. In this embodiment, based on an equivalent number of the third peptide as 1, and the equivalent number of the chlorine-containing inorganic salt can be, for example, at least 1,500 preferably. The aforementioned real-time monitoring salt exchange step can employ a UV detecting element to monitor specific absorption wavelength, for example, an absorption wavelength of 200 to 240 nm, preferably an absorption wavelength of 210 to 230 nm, so as to synchronously monitor the degree of the salt exchange. For clarification, if the aforementioned third solution system includes hydrochloric acid, then in a low-pH environment, amino ($NH_2$) at a C terminal of etelcalcetide is prone to deamidation to be degraded into hydroxyl (OH), which will generate impurities to reduce the purity of the final product.

The resulted etelcalcetide HCL is optionally subjected to a lyophilization step, so as to obtain a final product as shown in a formula (III-1) (SEQ ID NO:3), where m is 4-5 (i.e., $4 \leq m \leq 5$):

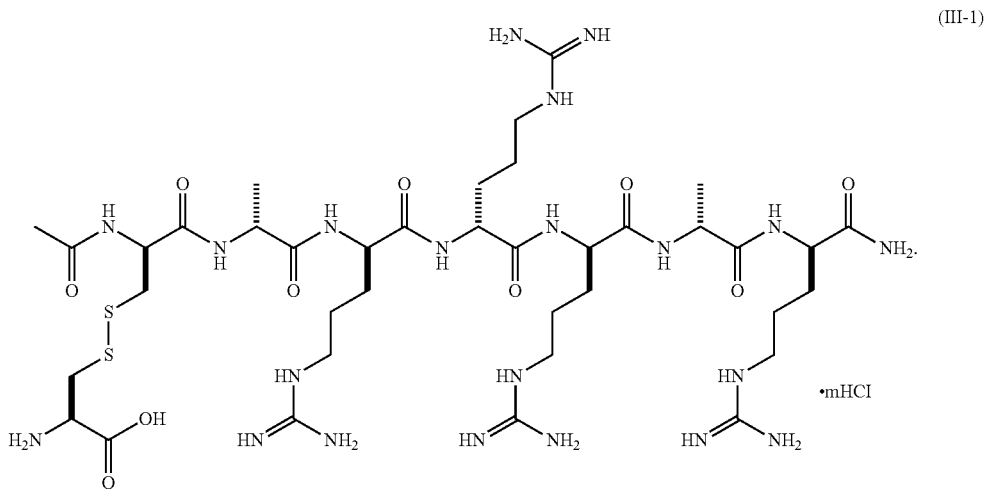

(III-1)

It should be noted that, in the method for synthesizing etelcalcetide HCL of the present invention, only one lyophilization step is needed to obtain high-purity and high-yield etelcalcetide HCL, thereby effectively improving the shortcomings of the conventional processes that need multiple lyophilization and thus is time-consuming.

The etelcalcetide HCL of the present invention can exist in a form of hydrate or solvate. In other embodiments, the aforementioned etelcalcetide HCL can be used in a medicinal composition, or together with existing drugs.

Thereinafter, it will be understood that particular configurations, aspects, examples, clauses and embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1-1: Synthesis of a Main-Chain Linear Segment of a Second Peptide (Ac-D-Cys-D-Ala-D-Arg-D-Arg-D-Arg-D-Ala-D-Arg-NH2)

In the EXAMPLE, Rink amide MBHA resin was used to perform synthesis with a stepwise Fmoc-solid phase peptide synthesizing strategy.

The Rink amide MBHA resin (10.00 g, replacement value 0.92 mmol/g) was soaked and swelled in DMAc (1 g/10 mL) for 15 min, and DMAc is filtered off. 20% piperidine [dissolved in DMAc (v/v) (1 g/6 mL)] was added and reacted for at least 10 min, and then the solution was removed; and the steps were repeated once. A TNBS reagent was used for detection, and a positive result indicated that the Fmoc removal reaction was completed. Next, the resin was rinsed once with DMAc, twice with IPA and then twice with DMAc, so as to remove the residual piperidine. The protected amino acid Fmoc-D-Arg(Pbf)-OH (1.5 eq.), Oxyma (1.5 eq.) and DIC (2.0 eq.) were dissolved and activated in DMAc, and then reacted with the resin at room temperature. A TNBS reagent was used for detection until a negative result indicated that a ligation reaction was completed. After the reaction was completed, the resin was rinsed four times with DMAc. According to the operation steps of Fmoc removal and ligation of the protected amino acids as aforementioned, other protected amino acids in the amino acid sequence were subjected to these reactions. The protected amino acids sequentially used in the above reactions were sequentially Fmoc-D-Ala-OH, Fmoc-D-Arg(Pbf)-OH, Fmoc-D-Arg(Pbf)-OH, Fmoc-D-Arg(Pbf)-OH, Fmoc-D-Ala-OH and Fmoc-D-Cys(Trt)-OH were used in order in the above reactions.

After the last removal of Fmoc, N-terminal acetylation was performed with acetic anhydride (4 eq.) and DIPEA (6 eq.) in DMAc, and a TNBS reagent as used for detection until a negative result indicates that the ligation reaction was completed. After the reaction was completed, the resin was sequentially rinsed once with DMAc, twice with IPA and twice with MTBE, and vacuum drying was performed to obtain a first peptide (29.29 g) bound to the resin, as shown in a formula (I-1):

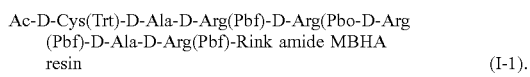

The first peptide (28.72 g) was added with TFA 180 mL/TIPS 6 mL/EDT 10 mL/H$_2$O$_4$ mL, and reacted for 2 h at room temperature, so as to remove the side-chain protecting group and the resin. Filtration was performed, and the filtrate was collected; the resin was rinsed with 68 mL of TFA, and then filtration was performed; and the two filtrates were combined. After the filtrate was cooled to 0-10° C., 540 mL of MTBE was added, and a solid was precipitated. After filtration, the solid was rinsed twice with MTBE, and vacuum drying was performed to obtain a white solid (9.72 g) of a linear segment of a second peptide, with purity of 76%, as shown in a formula (II-1):

Example 1-2: Synthesis of A Main-Chain Linear Segment of a Second Peptide (Ac-D-Cys-D-Ala-D-Arg-D-Arg-D-Arg-D-Ala-D-Arg-NH2)

In the EXAMPLE employs Rink amide AM resin to perform synthesis with a stepwise Fmoc-solid phase peptide synthesizing strategy.

The Rink amide AM resin (4.00 g, replacement value 0.66 mmol/g) was soaked and swelled in DMAc (1 g/10 mL) for 15 min, and DMAc was filtered off. 20% piperidine [dissolved in DMAc (v/v) (1 g/6 mL)] was added and reacted for at least 10 min, and then the solution was removed; and the steps were repeated once. A TNBS reagent was used for detection, and a positive result indicates that the Fmoc removal reaction was completed. Next, the resin was rinsed once with DMAc, twice with IPA and then twice with DMAc, so as to remove the residual piperidine. The protected amino acids Fmoc-D-Arg(Pbf)-OH (1.5 eq.), Oxyma (1.5 eq.) and DIC (2.0 eq.) were dissolved in DMAc for activation, and then reacted with the resin at room temperature. A TNBS reagent was used for detection until a negative result indicates that a ligation reaction was completed. After the reaction was completed, the resin was rinsed four times with DMAc. According to the aforementioned operation steps of Fmoc removal and ligation of the protected amino acids, reactions of other protected amino acids in the sequence were performed.

The protected amino adds used were sequentially Fmoc-D-Ala-OH, Fmoc-D-Arg(Pbf)-OH, Fmoc-D-Arg(Pbf)-OH, Fmoc-D-Arg(Pbf)-OH, FmocD-Ala-OH and Fmoc-D-Cys(Trt)-OH.

After last removal of Fmoc, N-terminal acetylation was performed in DMAc by using acetic anhydride (4 eq.) and DIPEA (6 eq.), and a TNBS reagent was used for detection until a negative result indicates that the ligation reaction was completed. After the reaction was completed, the resin was sequentially rinsed once with DMAc, twice with IPA and twice with MTBE, and vacuum drying was performed to obtain a first peptide (10.81 g) bound to the resin, as shown in a formula (I-2):

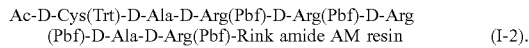

Ac-D-Cys(Trt)-D-Ala-D-Arg(Pbf)-D-Arg(Pbf)-D-Arg(Pbf)-D-Ala-D-Arg(Pbf)-Rink amide AM resin        (I-2).

The first peptide (10.80 g) was added with TFA 63 mL/TIPS 2.1 mL/EDT 3.5 mL/H$_2$O 1.4 mL, and reacted for 2 h at room temperature, so as to remove the side-chain protecting group and the resin. Filtration was performed, and the filtrate was collected; the resin was rinsed with 30 mL of TFA, and then filtration was performed; and the two filtrates were combined. After the filtrate was cooled to 0-10° C., 200 mL of MTBE was added, and a solid was separated out. After filtration, the solid was rinsed twice with MTBE, and vacuum drying was performed to obtain a white solid (2.87 g) of a linear segment of a second peptide, as shown in a formula (II-1):

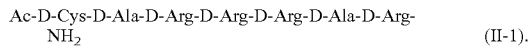

Ac-D-Cys-D-Ala-D-Arg-D-Arg-D-Arg-D-Ala-D-Arg-NH$_2$        (II-1).

Example 2-1: Preparation of A Crude Product of Etelcalcetide Trifluoroacetate The second peptide (7.44 g) was added with 1.38 g of L-/Cys(Pys)-OH, and the mixture was added into 59 ml of a second solution system in which a volume ratio of MTBE and ACN was 4/1, and stirred for at least 30 min at room temperature. The reaction was monitored with HPLC until the second peptide disappears; and after filtration, the collected solid was rinsed twice with MTBE, and vacuum drying was performed to obtain 7.27 g of a white solid, which was the crude product of etelcalcetide trifluoroacetate.

Example 2-2: Preparation of A Crude Product of Etelcalcetide Trifluoroacetate The second peptide (5.12 g) was added with 0.86 g of L-Cys(Pys)-OH and 20 ml of acetic acid, and the mixture was stirred for at least 30 min at room temperature. The reaction was monitored with HPLC until the second peptide disappears, and the reaction liquid was added into 125 mL of a second solution system of MTBE at room temperature; and after filtration, the collected solid was rinsed twice with MTBE, and vacuum drying was performed to obtain 5.98 g of a white solid, which was the crude product of etelcalcetide trifluoroacetate.

Example 2-3: Preparation of A Crude Product of Etelcalcetide Trifluoroacetate The second peptide (10.06 g) was added with 1.78 g of L-Cys(Pys)-OH, and the mixture was added into 80 ml of a second solution system in which a volume ratio of MTBE and IPA was 4/1, and stirred for at least 30 min at room temperature. The reaction was monitored with HPLC until the second peptide disappears; and after filtration, the collected solid was rinsed twice with MTBE, and vacuum drying was performed to obtain 9.70 g of a white solid, which was the crude product of etelcalcetide trifluoroacetate.

Example 2-4: Preparation of A Crude Product of Etelcalcetide Trifluoroacetate The EXAMPLE 2-4 was performed according to the method of the EXAMPLE 2-1, and the difference was that the second solution system of the EXAMPLE 2-4 was MTBE/methanol in a volume ratio of 4/1.

Comparative Example 2-1 and Comparative Example 2-2

The Comparative EXAMPLE 2-1 and Comparative EXAMPLE 2-2 were performed according to the method of the EXAMPLE 2-1, and the differences were that the second solution system of the Comparative EXAMPLE 2-1 was MTBE/DMAc in a volume ratio of 4/1 while the second solution system of the Comparative EXAMPLE 2-2 was MTBE/AcOH in a volume ratio of 4/1.

TABLE 2 was a comparison of the second solution systems of EXAMPLES 2-1 to 2-4 and Comparative EXAMPLES 2-1 to 2-2.

TABLE 2

| Second solution system | State of The Product | Filtration efficiency |
|---|---|---|
| EXAMPLE 2-1 | The solid was uniformly dispersed and non-stick | Easily transferred and filtered |
| EXAMPLE 2-2 | The solid was uniformly dispersed and non-stick | Easily transferred and filtered |
| EXAMPLE 2-3 | The solid was uniformly dispersed and non-stick | Easily transferred and filtered |
| EXAMPLE 2-4 | The solid was uniformly dispersed, non-stick, but relatively thin | Transferred and filtered with a relatively slow filtering speed |
| Comparative EXAMPLE 2-1 | The solid was as sticky as malt sugar | Hardly transferred and filtered |
| Comparative EXAMPLES 2-2 | The solid was as sticky as chewing gum | Hardly transferred and filtered |

Example 3: Purification Step

The crude product of etelcalcetide (2.3 g) obtained in the EXAMPLE 2 was dissolved in water, filtered with a 0.45 µm microfiltration membrane and then purified with a prepgrade high-performance liquid chromatography (HPLC) device, where the column filler was reversed-phase C18 silica gel, a mobile-phase system was a 0.1% aqueous solution of TFA plus a 0.1% solution of TFA in acetonitrile, and a gradient system was used for extraction and purification. Samples with purity of greater than 90.0% were collected, and the organic solvents were removed by reduced-pressure distillation, so as to obtain a purified aqueous solution of etelcalcetide trifluoroacetate (with a volume of about 890 mL), with purity of greater than 99.5%.

Example 4-1: Salt Exchange Step (NaCl)

The purified solution (with a volume of 205 mL and a concentration of 0.56 mg/mL) obtained in the EXAMPLE 3 was added with sodium chloride (molar ratio of NaCl/third peptide=1,536/1); after dissolution, the mixture flowed into a reversed-phase C18 silica gel column, extraction was performed with 100% water, the extracted samples were monitored and collected with a UV220 nm detecting element, and the white solid (116 mg) obtained by lyophilization was etelcalcetide HCL (SEQ ID NO: 3), where the purity was greater than 99.5%, the content of each single impurity was less than 0.1%, the residual amount of trifluoroacetic acid was 2,509 ppm, the content of chloride ions was 12% (w/w), and the total yield from the solid phase synthesis to the salt exchange and lyophilization was about 30-35%.

Example 4-2: Salt Exchange Step (NaCl)

The purified solution (with a volume of 210 mL and a concentration of 0.56 mg/mL) obtained in the EXAMPLE 3 was added with sodium chloride (molar ratio of NaCl/third peptide=2,093/1); after dissolution, the mixture flowed into a reversed-phase C18 silica gel column, extraction was performed with 100% water, the extracted samples were monitored and collected with a UV220 nm detecting element, and the white solid (113 mg) obtained by lyophilization was etelcalcetide HCL (SEQ ID NO: 3), where the purity was greater than 99.5%, the content of each single impurity was less than 0.1%, the residual amount of trifluoroacetic acid was 3,650 ppm, and the content of chloride ions was 13% (w/w).

Example 4-3: Salt Exchange Step (NaCl)

The purified solution (with a volume of 210 mL and a concentration of 0.56 mg/mL) obtained in the EXAMPLE 3 was added with sodium chloride (molar ratio of NaCl/third peptide=3,178/1); after dissolution, the mixture flowed into a reversed-phase C18 silica gel column, extraction was performed with 100% water, the extracted samples were monitored and collected with a UV220 nm detecting element, and the white solid (110 mg) obtained by lyophilization was etelcalcetide HCL (SEQ ID NO: 3), where the purity was greater than 99.5%, the content of each single impurity was less than 0.1%, the residual amount of trifluoroacetic acid was 1,764 ppm, and the content of chloride ions was 13% (w/w).

Example 4-4: Salt Exchange Step (KCl)

The purified solution (with a volume of 96 mL and a concentration of 1.26 mg/mL) obtained in the EXAMPLE 3 was added with potassium chloride (molar ratio of KCl/third peptide=1,978/1); after dissolution, the mixture flowed into a reversed-phase C18 silica gel column, extraction was performed with 100% water, the extracted samples were monitored and collected with a UV220 nm detecting element, and the white solid (112 mg) obtained by lyophilization was etelcalcetide HCL (SEQ ID NO:3), where the purity was greater than 99.5%, the content of each single impurity was less than 0.1%, the residual amount of trifluoroacetic acid was 2,424 ppm, and the content of chloride ions was 13% (w/w).

Example 4-6: Salt Exchange Step ($NH_4Cl$)

The purified solution (with a volume of 210 mL and a concentration of 0.54 mg/mL) obtained in the EXAMPLE 3 was added with ammonium chloride (molar ratio of NH4Cl/third peptide=2,003/1); after dissolution, the mixture flowed into a reversed-phase C18 silica gel column, extraction was performed with 100% water, the extracted samples were monitored and collected with a UV220 nm detecting element, and the white solid (112 mg) obtained by lyophilization was etelcalcetide HCL (SEQ ID NO: 3), where the purity was greater than 99.5%, the content of each single impurity was less than 0.1%, the residual amount of trifluoroacetic acid was 2,868 ppm, and the content of chloride ions was 13% (w/w).

Example 4-6: Salt Exchange Step ($CaCl_2$)

The purified solution (with a volume of 205 mL and a concentration of 0.6 mg/mL) was added with calcium chloride (molar ratio of CaCl2/third peptide=2,123/1); after dissolution, the mixture flowed into a reversed-phase C18 silica gel column, extraction was performed with 100% water, the extracted samples were monitored and collected with a UV220 nm detecting element, and the white solid (124 mg) obtained by lyophilization was etelcalcetide HCL (SEQ ID NO:3), where the purity was greater than 99.5%, the content of each single impurity was less than 0.1%, and the residual amount of trifluoroacetic acid was 1,669 ppm. The content of chloride ions was 12% (w/w).

Comparative Examples 4-1 to 4-3: Salt Exchange Step

The Comparative EXAMPLES 4-1 to 4-3 were performed according to the method of the EXAMPLE 4-1, and the difference was that, in the Comparative EXAMPLE 4-1, the purified solution obtained in the EXAMPLE 3 was not added with a chlorine-containing inorganic salt for a salt exchange step. In the Comparative EXAMPLE 4-2, the purified solution obtained in the EXAMPLE 3 was added with sodium chloride (molar ratio NaCl/third peptide=18711) for a salt exchange step. In the Comparative EXAMPLE 4-3, the purified solution obtained in the EXAMPLE 3 was added with sodium chloride (molar ratio NaCl/third peptide=1,029/1) for a salt exchange step.

Comparison between the salt exchange steps of the EXAMPLES 4-1 to 4-6 and the Comparative EXAMPLES 4-1 to 4-3 was shown in TABLE 3, where, if the residual amount of TFA was less than 5,000 ppm, the content of chloride ions would comply with relevant standards.

TABLE 3

| Salt exchange step | Solid was freeze-dried after the salt exchange step | | | Yield |
|---|---|---|---|---|
| | Residual amount of TFA (ppm) | Cl content (wt. %) | HCl amount (mean or m value) in the formula (III-1) | Salt exchange and lyophilization |
| Comparative EXAMPLE 4-1 | N/A | N/A | N/A | 0% |
| Comparative EXAMPLE 4-2 | N/A | N/A | N/A | 60% |
| Comparative EXAMPLE 4-3 | 49,557 | 11% | 3.7 | 89% |
| EXAMPLE 4-1 | 2,509 | 12% | 4.1 | 100% |
| EXAMPLE 4-2 | 3650 | 13% | 4.4 | 96% |
| EXAMPLE 4-3 | 1,764 | 13% | 4.4 | 94% |
| EXAMPLE 4-4 | 2,424 | 13% | 4.4 | 93% |
| EXAMPLE 4-5 | 2,868 | 13% | 4.4 | 99% |
| EXAMPLE 4-6 | 1,669 | 12% | 4.1 | 100% |

Example 4-7: Real-Time Monitoring Salt Exchange Step

Figure 1B:
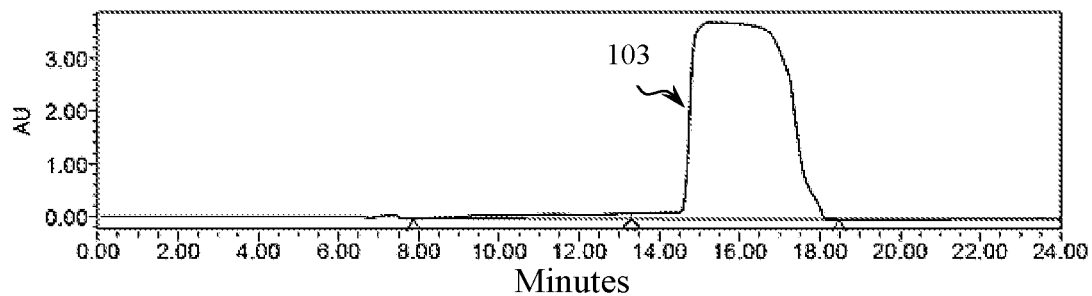
Figure 1C:
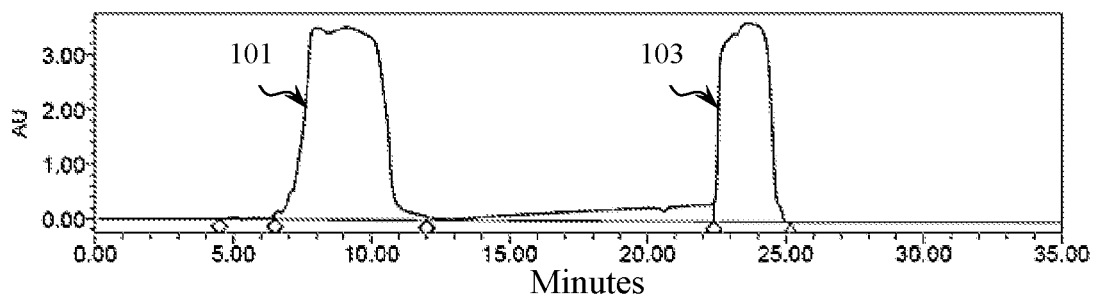

Please refer to FIGS. 1A-1C, which respectively showed the HPLC spectrograms of a real-time monitoring salt exchange step performed in the EXAMPLE 4-2 (FIG. 1A), Comparative EXAMPLE 4-1 (FIG. 1B) and Comparative EXAMPLE 4-2 (FIG. 1C) of the present invention, where the peak indicated by the arrow 101 referred to etelcalcetide HCL (SEQ ID NO:3), the peak indicated by the arrow 103 referred to TFA salt of etelcalcetide (SEQ ID NO:3), the peak indicated by the arrow 105 referred to impurities, and AU referred to an arbitrary unit.

The results of FIGS. 1A-1C indicated that, the method of the present Invention really could employ a UV220 nm detecting element to perform a real-time monitoring salt exchange step, and EXAMPLES could obtain high-yield etelcalcetide HCL 101, thereby facilitating mass production. In contrast, the Comparative EXAMPLE 4-1 could detect little etelcalcetide HCL, but a large amount of TFA salt of etelcalcetide 103. Despite some etelcalcetide HCL 101 in the Comparative EXAMPLE 4-2, there was a large amount of TFA salt of etelcalcetide 103.

Figure 2:
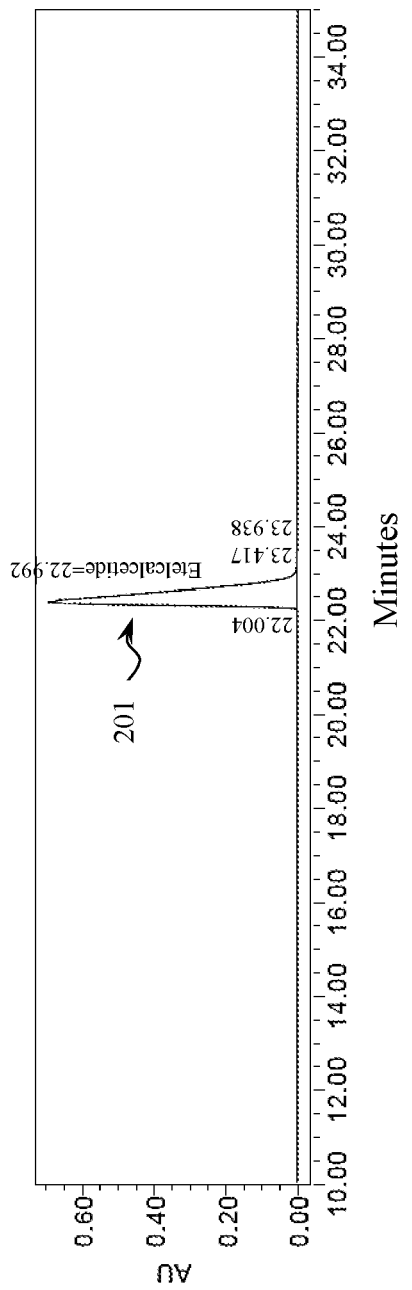
FIG. 2 illustrates the HPLC spectrogram of etelcalcetide HCL after a purification step by column chromatography according to Embodiment 4-2 of the present invention.

Please referred to FIG. 2, which illustrated the HPLC spectrogram of etelcalcetide HCL after a purification step by column chromatography according to EXAMPLE 4-2 of the present invention, where the arrow 201 indicated to an absorption peak of etelcalcetide HCL, and relevant values in FIG. 2 were shown in TABLE 4. The results of the FIG. 2 and TABLE 4 indicated that, the etelcalcetide HCL obtained by the method of the present invention exactly had high purity (99.93%).

TABLE 4

| Name | Retention time (minute) | Peak Height | Area | Area % |
|---|---|---|---|---|
| Etelcalcetide | 22.392 | 698,055 | 13,532,688 | 99.93 |

In summary, the aforementioned specific amino acids, specific protecting groups, specific treating steps, solution systems with specific compositions, specific analysis models or specific evaluation methods were only exemplary to describe a method for preparing etelcalcetide HCL. However, those of common knowledge in the technical field of the present invention should understand that other amino acids, other protecting groups, other treating steps, solution systems of other compositions, other analysis models or other evaluation methods, etc., also can be applied to the method for preparing etelcalcetide HCL, without departing from the spirit and scope of the present invention. For example, a free-form second peptide prepared by other method can be used to perform a coupling reaction as well as a real-time monitoring salt exchange step, thereby simplifying the process and being advantageously applied in mass production of etelcalcetide HCL.

According to the aforementioned embodiments, in the method for preparing etelcalcetide HCL of the present invention, the TFA salt of etelcalcetide is not or hardly dissolved in the second solution system, and the TFA salt of etelcalcetide is converted to etelcalcetide HCL by using a hydrochloric acid-free third solution system. Therefore, the present method provides a simplified process and the etelcalcetide HCL with high purity and yield, for being advantageously applied in mass production of etelcalcetide HCL.

Although the present invention has been described in considerable detail with reference to certain embodiments thereof, other embodiments are possible. Therefore, the spirit and scope of the appended claims should not be limited to the description of the embodiments contained herein.

SEQUENCE LISTING

```
Sequence total quantity: 3
SEQ ID NO: 1          moltype = AA  length = 7
FEATURE               Location/Qualifiers
source                1..7
                      mol_type = protein
                      organism = synthetic construct
MOD_RES               1
                      note = Cys-Cys disulfide bond to Cys
                      note = N-terminal acetylation
                      note = D-Cys[Trt]
MOD_RES               2
                      note = D-Ala
MOD_RES               3
                      note = D-Arg(Pbf)
MOD_RES               4
                      note = note = D-Arg(Pbf)
MOD_RES               5
                      note = D-Arg(Pbf)
MOD_RES               6
                      note = D-Ala
```

```
MOD_RES                 7
                        note = D-Arg(Pbf)
                        note = C-terminal amination
SEQUENCE: 1
CARRRAR                                                                              7

SEQ ID NO: 2            moltype = AA  length = 7
FEATURE                 Location/Qualifiers
source                  1..7
                        mol_type = protein
                        organism = synthetic construct
SEQUENCE: 2
CARRRAR                                                                              7

SEQ ID NO: 3            moltype = AA  length = 7
FEATURE                 Location/Qualifiers
source                  1..7
                        mol_type = protein
                        organism = synthetic construct
MOD_RES                 1
                        note = D-Cys
                        note = Cys-Cys disulfide bond to Cys
                        note = N-terminal acetylation
MOD_RES                 2
                        note = D-Ala
MOD_RES                 3
                        note = D-Arg
MOD_RES                 4
                        note = D-Arg
MOD_RES                 5
                        note = D-Arg
MOD_RES                 6
                        note = D-Ala
MOD_RES                 7
                        note = D-Arg
                        note = C-terminal amidation
SEQUENCE: 3
CARRRAR                                                                              7
```

What is claimed is:

1. A method for preparing etelcalcetide hydrochloride (HCL), comprising:

performing a solid-phase synthesis step to obtain a first peptide shown in a formula (I) (SEQ ID NO:1), wherein the first peptide is a resin-bound peptide, Ac of the formula (I) represents an acetyl group, X represents a first side-chain protecting group, and Y represents a second side-chain protecting group:

Ac-D-Cys(X)-D-Ala-D-Arg(Y)-D-Arg(Y)-D-Arg(Y)-
   D-Ala-D-Arg(Y)—NH-resin                              (I);

removing the first side-chain protecting group (X) and the second side-chain protecting group (Y) of the first peptide by using a first solution system, and separating the first peptide from the resin, thereby obtaining a second peptide shown in a formula (II) (SEQ ID NO: 2), wherein the first solution system consists of trifluoroacetic acid (TFA), triisopropyl silane (TIS), ethanedithiol (EDT) and water:

Ac-D-Cys-D-Ala-D-Arg-D-Arg-D-Arg-D-Ala-D-Arg-
   NH2                                                  (II);

coupling L-Cys(Z)—OH to the D-Cys residue of the second peptide in a second solution system, and forming a disulfide bond, thereby obtaining TFA salt of etelcalcetide, wherein the etelcalcetide consists of a third peptide (SEQ ID NO:3), the TFA salt of etelcalcetide is not dissolved in the second solution system, and Z represents a side-chain activating group;

performing a purification step by column chromatography on the TFA salt of etelcalcetide, thereby removing the second solution system; and performing a real-time monitoring salt exchange step on the TFA salt of the etelcalcetide by using a third solution system, thereby obtaining the etelcalcetide HCL, wherein the third solution system comprises a chlorine-containing inorganic salt but excludes hydrochloric acid.

2. The method for preparing etelcalcetide HCL of claim 1, wherein the first side-chain protecting group (X) is Trt, the second side-chain protecting group (Y) is Pbf, and the side-chain activating group (Z) is Pys.

3. The method for preparing etelcalcetide HCL of claim 1, wherein the resin comprises amide resin, and the C terminal of the first peptide is immobilized to the amino group of the amide resin.

4. The method for preparing etelcalcetide HCL of claim 1, wherein the second solution system comprises a lower alkyl ether, and the lower alkyl ether comprises methyl tert-butyl ether (MTBE), diethyl ether (DEE), ethyl tert-butyl ether (ETBE) or tert-amyl methyl ether (TAME).

5. The method for preparing etelcalcetide HCL of claim 4, wherein the second solution system further comprises acetonitrile (ACN), a lower alcohol or any combination thereof.

6. The method for preparing etelcalcetide HCL of claim 5, wherein the lower alcohol comprises methanol, ethanol, 1-propanol, isopropanol (IPA), 1-butanol, 2-butanol or tert-butanol (TBA).

7. The method for preparing etelcalcetide HCL of claim 1, wherein based on a molar equivalent number of the third peptide (SEQ ID NO:3) as 1, the molar equivalent number of the chlorine-containing inorganic salt is at least 1,500.

8. The method for preparing etelcalcetide HCL of claim 1, wherein the chlorine-containing inorganic salt comprises NaCl, KCl, CaCl$_2$ or NH$_4$Cl.

9. A method for preparing etelcalcetide HCL, comprising:
providing a first peptide shown in a formula (II), wherein Ac of the formula (II) (SEQ ID NO: 2) represents an acetyl group, and the second peptide is in a free form:

Ac-D-Cys-D-Ala-D-Arg-D-Arg-D-Arg-D-Ala-D-Arg-NH2  (II);

performing a coupling reaction by using a first solution system, so that L-Cys(Z)—OH is coupled to the D-Cys residue of the first peptide and a disulfide bond is formed, thereby obtaining TFA salt of etelcalcetide, wherein the etelcalcetide consists of a second peptide (SEQ ID NO:3), the TFA salt of etelcalcetide is not dissolved in the first solution system, and Z represents a side-chain activating group;
performing a solid-liquid separation step and a purification step by column chromatography on the TFA salt of etelcalcetide, thereby removing the first solution system and obtaining the TFA salt of etelcalcetide, wherein the solid-liquid separation step comprises a filtration step; and
performing a real-time monitoring salt exchange step on the TFA salt of etelcalcetide by using a second solution system, thereby obtaining the etelcalcetide HCL, wherein the second solution system comprises a chlorine-containing inorganic salt, and the chlorine-containing inorganic salt comprises NaCl, KCl, CaCl$_2$ or NH$_4$Cl but excludes hydrochloric acid.

10. The method for preparing etelcalcetide HCL of claim 9, wherein the first solution system comprises a lower alkyl ether, and the lower alkyl ether comprises methyl tert-butyl ether (MTBE), diethyl ether (DEE), ethyl tert-butyl ether (ETBE) or tert-amyl methyl ether (TAME).

11. The method for preparing etelcalcetide HCL of claim 10, wherein the first solution system further comprises acetonitrile (ACN), a lower alcohol or any combination thereof.

12. The method for preparing etelcalcetide HCL of claim 11, wherein the lower alcohol comprises methanol, ethanol, 1-propanol, isopropanol (IPA), 1-butanol, 2-butanol or tert-butanol (TBA).

13. The method for preparing etelcalcetide HCL of claim 9, wherein based on a molar equivalent number of the second peptide (SEQ ID NO:3) as 1, the molar equivalent number of the chlorine-containing inorganic salt is at least 1,500.

14. The method for preparing etelcalcetide HCL of claim 9, wherein the side-chain activating group (Z) is Pys.

* * * * *